(12) United States Patent
Tarkka et al.

(10) Patent No.: US 9,311,453 B2
(45) Date of Patent: Apr. 12, 2016

(54) UTILIZING TIME-TO-POSITIVITY TO GENERATE TREATMENT RECOMMENDATIONS

(75) Inventors: Susan M. Tarkka, Kansas City, MO (US); Timothy S. Kelly, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 2201 days.

(21) Appl. No.: 11/609,108

(22) Filed: Dec. 11, 2006

(65) Prior Publication Data

US 2008/0140372 A1 Jun. 12, 2008

(51) Int. Cl.
| | |
|---|---|
| *G01N 33/48* | (2006.01) |
| *G01N 33/50* | (2006.01) |
| *G06F 19/00* | (2011.01) |
| *G06F 19/12* | (2011.01) |
| *G06F 19/24* | (2011.01) |

(52) U.S. Cl.
CPC .............. *G06F 19/366* (2013.01); *G06F 19/12* (2013.01); *G06F 19/24* (2013.01); *G06F 19/3437* (2013.01)

(58) Field of Classification Search
None
See application file for complete search history.

(56) References Cited

U.S. PATENT DOCUMENTS

| | | | | |
|---|---|---|---|---|
| 4,220,715 A | * | 9/1980 | Ahnell | ............................. 435/34 |
| 2003/0055679 A1 | * | 3/2003 | Soll et al. | ........................... 705/2 |
| 2004/0072732 A1 | * | 4/2004 | Jabes et al. | ........................ 514/8 |
| 2004/0257227 A1 | * | 12/2004 | Berry | ............................ 340/540 |
| 2005/0038326 A1 | * | 2/2005 | Mathur | ........................ 600/300 |

OTHER PUBLICATIONS

Pittet et al. Microbiological factors influencing the outcome of nosocomial bloodstream infections: A 6-year validated, population-based model. Clinical Infectious Diseases, 1997, vol. 24, pp. 1068-1078.*
Doern et al. Clinical impact of rapid in vitro susceptibility testing and bacterial identification. Journal of Clinical Microbiology, 1994, vol. 32, pp. 1757-1762.*
Raymond Ruimy, MD, PhD, Laurence Armand-Lefevre, PharMD, and Antoine Andremont, MD, PhD, "Short time to positivity in blood culture with clustered gram-positive cocci on direct smear examination is highly predictive of *Staphylococcus aureus*," Paris, France, Jun. 2005.

* cited by examiner

*Primary Examiner* — Russell S Negin
(74) *Attorney, Agent, or Firm* — Shook, Hardy & Bacon L.L.P.

(57) ABSTRACT

Computerized methods and systems, and computer-readable media having computer-executable instructions embodied thereon, for utilizing a time-to-positivity associated with a blood culture to generate at least one treatment recommendation are provided. Methods according to embodiments of the present invention may include receiving an indication that a blood culture is positive for the presence of a particular bacterium, determining a time-to-positivity for the presence of the bacterium, and automatically generating at least one treatment recommendation utilizing the time-to-positivity. If desired, the method may further include one or more of receiving verification of the indication that the blood culture is positive for the presence of the bacterium in question and communicating the positivity determination as appropriate, e.g., utilizing alerts.

14 Claims, 5 Drawing Sheets

UTILIZING TIME-TO-POSITIVITY TO GENERATE TREATMENT RECOMMENDATIONS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

Time-to-positivity (TTP) is an important predictive indicator of the severity of potential blood borne infections. For instance, it has been shown that organisms of significant medical importance turn positive in continuous blood monitoring systems more quickly than commonly known contaminants. While common contaminants can represent a challenge since, e.g., they can cause sepsis in premature infants, immuno-compromised hosts and in hospitalized patients with intravascular devices (e.g., catheters), more often than not, contaminants simply represent a breakdown in the technique of collecting a blood culture specimen. If a common contaminant is isolated in only one blood culture bottle from a peripheral blood draw, it is generally not necessary to treat the patient with antibiotics. However, if an organism of significant medical importance is similarly isolated, the most effective patient care option will typically be to begin antibiotic therapy as quickly as possible.

BRIEF SUMMARY

Embodiments of the present invention relate to utilizing time-to-positivity determinations to generate treatment recommendations. "Time-to-positivity", as the term is utilized herein, refers to the time it takes for a blood culture having a particular bacterium present therein, to generate a detectable positive indication of the bacterium's presence. It will be understood by those of ordinary skill in the art that a number and variety of instruments are commercially available for detecting the presence of one or more bacteria and that embodiments of the present invention are not limited to use of any particular instrument. Likewise, indicators indicating a bacterium has been detected and methods and systems for detecting the time-to-positivity for the bacterium may vary from instrument to instrument. Embodiments of the present invention are not limited to any particular indicator or detection method/system except where explicitly set forth herein.

Embodiments of the present invention are directed to computer-readable media having computer-executable instructions embodied thereon for performing methods for utilizing a time-to-positivity associated with a blood culture to generate treatment recommendations. In one embodiment the method includes receiving an indication that the blood culture is positive for the presence of a particular bacterium, determining the time-to-positivity for the presence of the bacterium, and automatically generating at least one treatment recommendation utilizing the determined time-to-positivity. If desired, the method may further include one or more of receiving verification of the indication that the blood culture is positive for the presence of the bacterium in question and automatically generating at least one alert indicating that a treatment recommendation(s) has been generated.

Additional embodiments of the present invention are directed to methods for utilizing a time-to-positivity associated with a blood culture to generate at least one treatment recommendation. In one embodiment, the method includes receiving the time-to-positivity for the presence of a bacterium associated with the blood culture, wherein the time-to-positivity is received directly from a positivity-detecting instrument, and automatically generating at least one treatment recommendation utilizing the directly-received time-to-positivity. If desired, the method may further include one or more of receiving verification of the indication that the blood culture is positive for the presence of the bacterium in question and automatically generating at least one alert indicating that a treatment recommendation(s) has been generated.

Embodiments of the present invention are further directed to computing systems for utilizing a time-to-positivity associated with a blood culture to generate at least one treatment recommendation. In one embodiment, the system includes a time-receiving module configured to receive an indication of a plurality of times associated with the blood culture, a determining module in communication with the time-receiving module and configured to determine the time-to-positivity for the presence of a bacterium associated with the blood culture utilizing at least two times received by the time-receiving module, and a recommendation-generating module in communication with the determining module and configured to automatically generate at least one treatment recommendation utilizing the determined time-to-positivity. If desired, the system may further include a verification-receiving module in communication with the recommendation-generating module and configured to receive a verification of the presence of the bacterium associated with the blood culture before the at least one treatment recommendation is generated and/or an alert-generating module in communication with the recommendation-generating module and configured to automatically generate at least one alert indicating that at least one treatment recommendation has been generated.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide computerized methods and systems, and computer-readable media having computer-executable instructions embodied thereon, for utilizing a time-to-positivity associated with a blood culture to generate at least one treatment recommendation. Embodiments of the present invention further provide computerized methods and systems, and computer-readable media having computer-executable instructions embodied thereon, for communicating positivity determinations as appropriate, e.g., utilizing alerts. Numerous advantages are realized utilizing embodiments of the present invention. For instance, health care personnel are aided in making more effective patient care decisions, the costs for treating infections are better contained, and support is provided for appropriate selection of anti-infective therapy. Additionally, diagnoses of certain conditions, e.g., septicemia, are made easier.

An exemplary operating environment for embodiments of the present invention is described below.

Figure 1:
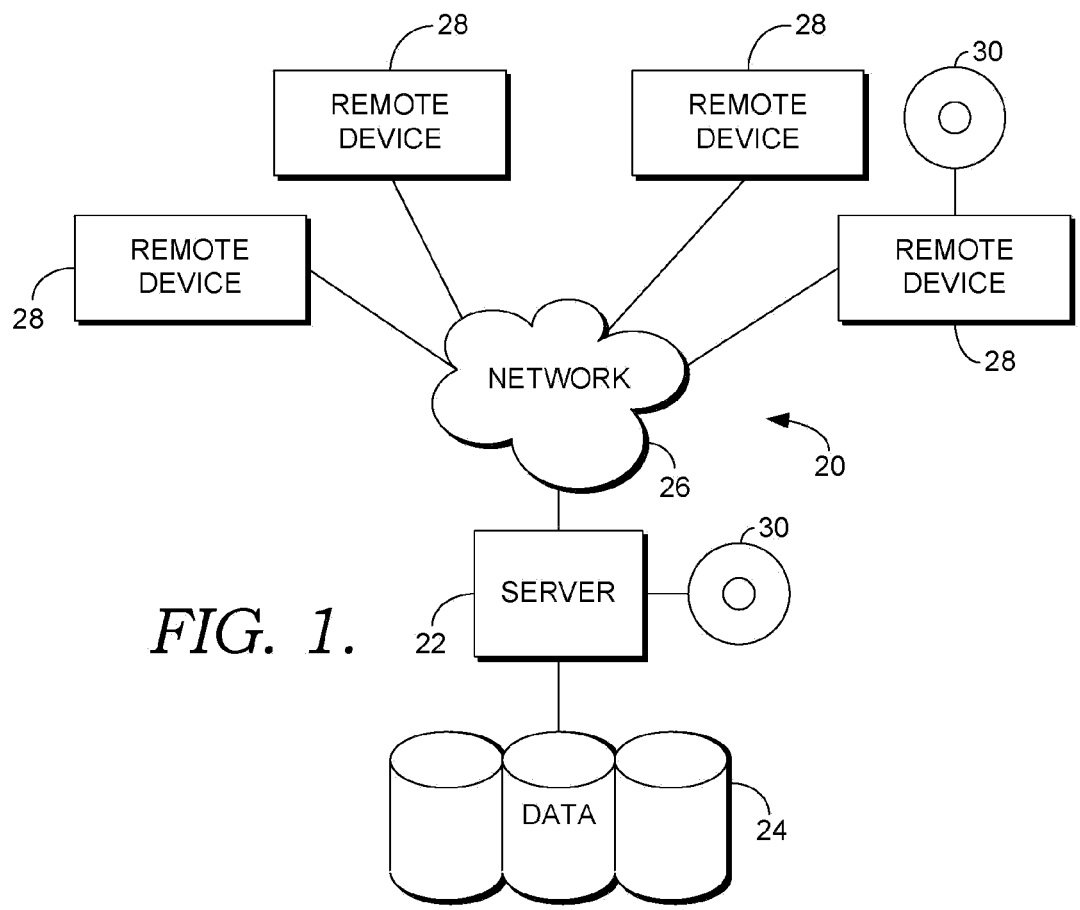
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system environment, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer-readable media, for instance, database cluster 24 and/or computer-readable disk 30. Computer-readable media can be any available media that may be accessed by server 22, and includes volatile and nonvolatile media, as well as removable and non-removable media. By way of example, and not limitation, computer-readable media may include computer storage media and communication media. Computer storage media may include, without limitation, volatile and nonvolatile media, as well as removable and nonremovable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the server 22.

The server 22 may operate in a computing network 26 using logical connections to one or more remote computing devices 28. Remote computing devices 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, an infection control professional, a treating physician or physicians, specialists such as infectious disease physicians, surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computing devices 28 may also be physically located in non-traditional medical care environments so that the entire health care community may be capable of integration on the network. The remote computing devices 28 may be personal computers, servers, routers, network PCs, peer devices, other common network nodes, or the like, and may include some or all of the elements described above in relation to the server 22. The devices can be personal digital assistants or other like devices.

Exemplary computing networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, on any of the remote computing devices 28, or on one or more removable computer-readable media 30. For example, and not by way of limitation, various application programs may reside on the memory associated with any one or more of the remote computing devices 28. It will be appreciated by those of ordinary skill in the art that the network connections shown are exemplary and other means of establishing a communications link between the computing devices (e.g., server 22 and remote computing devices 28) may be utilized.

In operation, a user may enter commands and information into the server 22 or convey the commands and information to the server 22 via one or more of the remote computing devices 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote health care device to the server 22. In addition to a monitor, the server 22 and/or remote computing devices 28 may include other peripheral output devices, such as speakers and a printer.

Although many other internal components of the server 22 and the remote computing devices 28 are not shown, those of ordinary skill in the art will appreciate that such components and their interconnection are well known. Accordingly, additional details concerning the internal construction of the server 22 and the remote computing devices 28 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of health care-related orders. As contemplated by the language above, the methods and systems of embodiments of the present invention may also be implemented on a stand-alone desktop, personal computer, or any other computing device used in a health care environment or any of a number of other locations.

As previously mentioned, embodiments of the present invention relate to utilizing a time-to-positivity associated with a blood culture to generate at least one treatment recommendation. Embodiments of the present invention further relate to communicating time-to-positivity determinations as appropriate, e.g., utilizing alerts.

Figure 2:
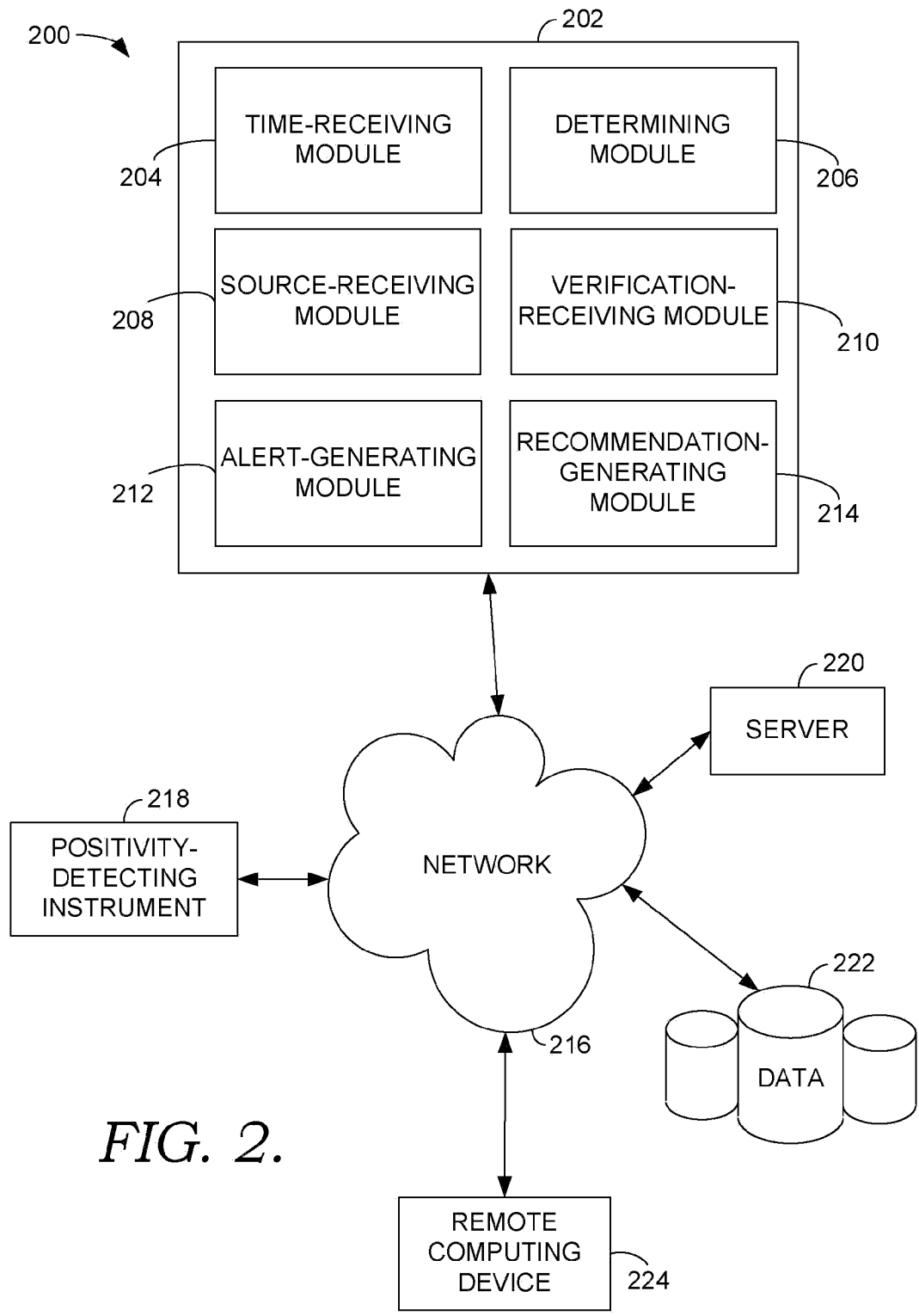
FIG. 2 is a block diagram of an exemplary computing system for utilizing time-to-positivity associated with a blood culture to generate at least one treatment recommendation, and for communicating such treatment recommendations as appropriate, in accordance with an embodiment of the present invention.

Referring to FIG. 2, a block diagram is illustrated that shows an overall system architecture 200 for utilizing a time-to-positivity associated with a blood culture to generate treatment recommendations and, if desired, to communicate such treatment recommendations as appropriate, for instance, utilizing alerts. It will be understood and appreciated by those of ordinary skill in the art that the overall system architecture 200 shown in FIG. 2 is merely an example of one suitable computing environment and is not intended to suggest any limitation as to the scope of use or functionality of the present invention. Neither should the overall system architecture 200 be interpreted as having any dependency or requirement related to any single component/module or combination of components/modules illustrated therein.

System 200 includes a user device 202 connected to a positivity-detecting instrument 218, a remote computing device 224, a server 220 and a database cluster 222 via a network 216. Each of the user device 202, the remote computing device 224, and the server 220 shown in FIG. 2 may be any type of computing device, such as, for example, computing device 100 described above with reference to FIG. 1. By way of example only and not limitation, each of the user device 202, the remote computing device 224, and/or the server 220 may be a personal computer, desktop computer, laptop computer, handheld device, consumer electronic device, and the like. It should be noted, however, that the invention is not limited to implementation on such computing devices, but may be implemented on any of a variety of different types of computing devices within the scope of embodiments of the present invention.

As shown in FIG. 2, the user device 202 includes a time-receiving module 204, a source-receiving module 208, a determining module 206, a verification-receiving module 210, a recommendation-generating module 214 and an alert-generating module 212 for implementing embodiments of the present invention. In some embodiments, the modules 204, 206, 208, 210, 212, and 214 may be implemented as stand-alone applications. In other embodiments, the modules 204, 206, 208, 210, 212, and 214 may be integrated directly into the operating system for the user device 202. It will be understood by those skilled in the art that the modules 204, 206, 208, 210, 212, and 214 illustrated in FIG. 2 are exemplary in nature and in number and should not be construed as limiting. Any number of modules may be employed to achieve the desired functionality within the scope of embodiments of the present invention.

The time-receiving module 204 is configured to receive an indication of a plurality of times associated with a blood culture. Such times may include, without limitation, a time at which a blood sample utilized to generate a blood culture is taken, a time at which the blood culture is inoculated (i.e., introduced into the culture media), a time at which a blood culture is received by a positivity-detecting instrument (e.g., positivity-detecting instrument 218), a time at which a blood culture generates a positive result for the presence of a particular bacterium, and a time at which a verification of a positive result for the presence of a particular bacterium is received. Such times may be manually input into the user device 202 by, for instance, a laboratory technologist or other health care personnel, or may be received directly from a positivity-detecting instrument (e.g., positivity-detecting instrument 218), for instance, via network 216. Any and all such variations are contemplated to be within the scope of embodiments of the present invention.

It will be understood and appreciated by those of ordinary skill in the art that the time-receiving module 204 may be configured to receive (manually or via network 216) an indication of a variety of additional times, as desired, and such variations are contemplated to be within the scope of embodiments hereof.

The source-receiving module 208 is configured to receive an indication of the source of a blood sample utilized to generate a blood culture. The source may be, for instance, from a peripheral line, from a central line, from a direct venous draw, or any other lineal attachment. Blood sample collection methods are well known to those of ordinary skill in the art and, accordingly, are not further described herein.

The determining module 206 is in communication with the time-receiving module 204 and is configured to determine a time-to-positivity for the presence of a particular bacterium associated with a blood culture utilizing at least two of the plurality of times received by the time-receiving module 204. For instance, and not by way of limitation, the determining module 206 may be configured to determine a time-to-positivity for the presence of a particular bacterium associated with a blood culture by determining a difference between a time at which a blood culture generates a positive result for the presence of a particular bacterium and a time at which a blood sample utilized to generate the blood culture is taken, a difference between a time at which a blood culture generates a positive result for the presence of a particular bacterium and a time at which the blood culture is inoculated, a difference between a time at which a blood culture generates a positive result for the presence of the particular bacterium and a time at which the blood culture is received by a positivity-detecting instrument (e.g., positivity-detecting instrument 218), a difference between a time at which a verification of a positive result for the presence of a particular bacterium is received and a time at which a blood sample utilized to generate the blood culture is taken, a difference between a time at which a verification of a positive result for the presence of a particular bacterium is received and a time at which the blood culture is inoculated, and a difference between a time at which a verification of a positive result for the presence of the particular bacterium is received and a time at which the blood culture is received by a positivity-detecting instrument (e.g., positivity-detecting instrument 214).

The verification-receiving module 210 is in communication with the determining module 206 and the recommendation-generating module 214 and is configured to receive verification, e.g., from a laboratory technologist, of a detected positivity result. In one embodiment, the recommendation-generating module 214 will not generate treatment recommendation(s) (as more fully described below) absent a verification indication.

The recommendation-generating module 214 is in communication with the source-receiving module 208 and the determining module 206 and is configured to automatically generate at least one treatment recommendation utilizing the determined time-to-positivity and the source of the blood sample, if known. For instance, if the time-to-positivity is determined to be in a first range, the recommendation-generating module 214 may recommend continuing antibiotic therapy or altering antibiotic therapy to an antibiotic more targeted to the bacterium in question. Alternatively, if the time-to-positivity is determined to be in a second range (different from the first range), and the source of the blood sample is peripheral, the recommendation-generating module 214 may recommend ceasing antibiotic therapy.

The recommendation-generating module 214 is further configured to communicate generated treatment recommendations (as well as the data utilized to make such recommendations, if desired) to a database 222 for storage (via network 216). In one embodiment, such recommendations may be stored in association with a patient's electronic medical record as part of an integrated electronic health care system. It will be understood and appreciated by those of ordinary skill in the art that database 222 may be a single database (not shown) or a database cluster as shown and may be a stand alone component or integrated with either server 220 or user device 202, or any combination thereof. Additionally, in some embodiments, the server 220 may be a plurality of servers (not shown) or may not be present in the system at all. Any and all such variations are contemplated to be within the scope of embodiments hereof.

The alert-generating module 212 is in communication with the recommendation-generating module 214 and is configured to automatically generate at least one alert indicating that a treatment recommendation has been generated. Such alert may be communicated (e.g., via network 216) and received, for instance, by a physician or other health care provider on remote computing device 224.

It will be understood and appreciated by those of ordinary skill in the art that one or more of the time-receiving module 204, the source-receiving module 208, the determining module 206, the verification-receiving module 210, the recommendation-generating module 214, and the alert-generating module 212 may be associated with the positivity-detecting instrument 218 rather than, or in addition to, the user device 202. Any and all such variations are contemplated to be within the scope of embodiments of the present invention.

Figure 3:
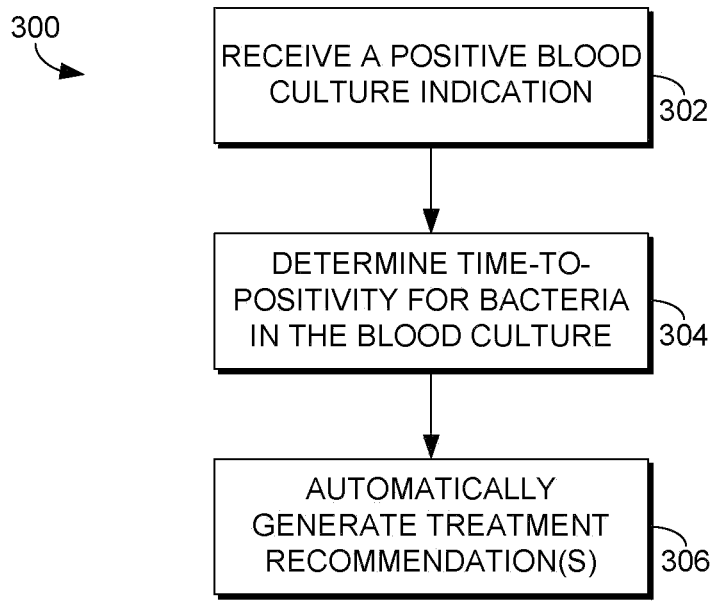
FIG. 3 is a flow diagram illustrating a method for utilizing time-to-positivity associated with a blood culture to generate at least one treatment recommendation, in accordance with an embodiment of the present invention.

Turning to FIG. 3, a flow diagram is illustrated that shows a method 300 for utilizing time-to-positivity associated with a blood culture to generate at least one treatment recommendation, in accordance with an embodiment of the present invention. Initially, as indicated at block 302, a positive blood culture indication is received, e.g., by positivity-detecting instrument 218 of FIG. 2. Next, as indicated at block 304, a time-to-positivity is determined for the bacterium that caused the positive result, for instance, utilizing determining module 206 of FIG. 2. Subsequently, as indicated at block 306, one or more treatment recommendations is generated utilizing the determined time-to-positivity, e.g., utilizing recommendation-generating module 214 of FIG. 2.

Figure 4:
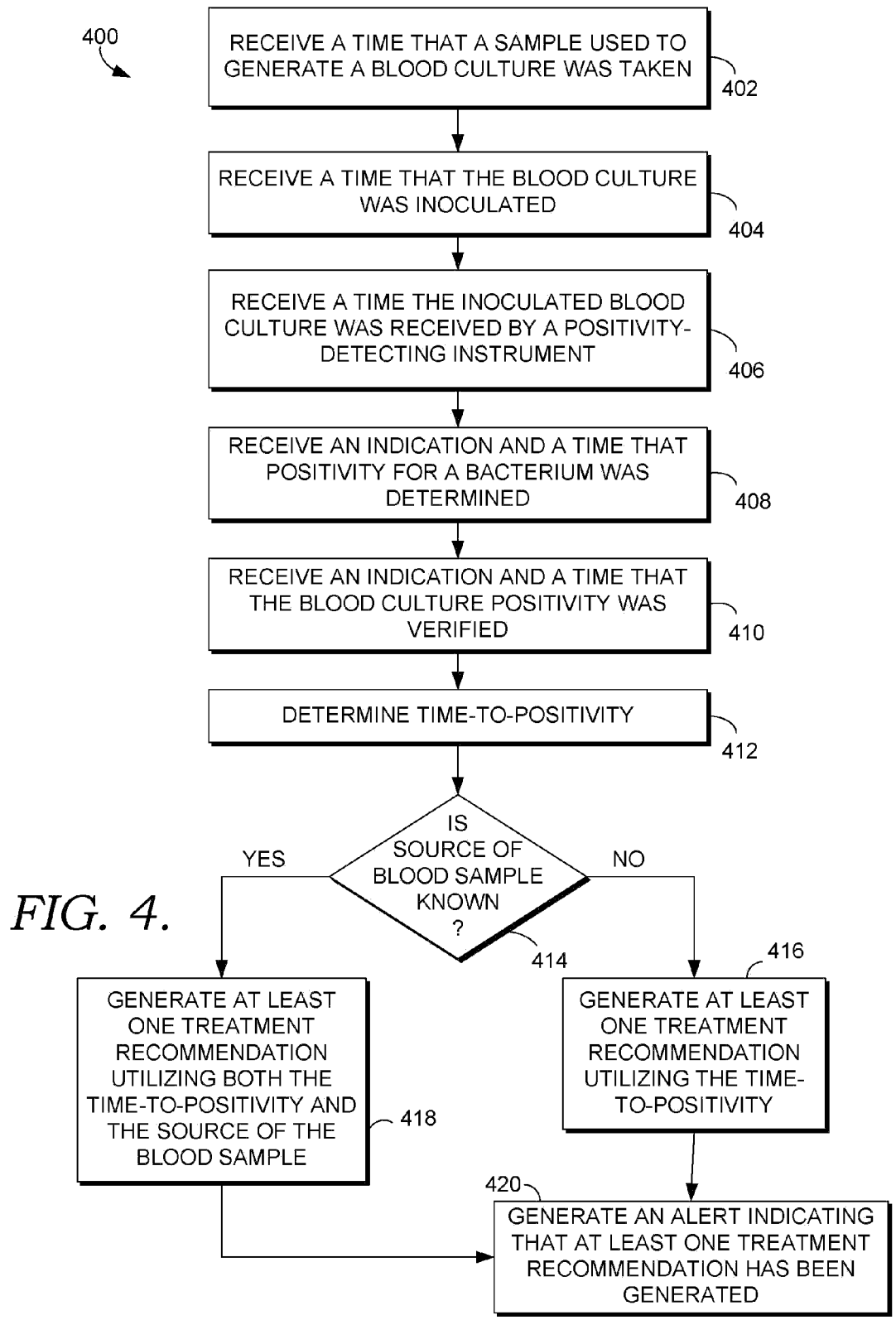
FIG. 4 is a flow diagram illustrating a method for utilizing time-to-positivity associated with a blood culture to generate at least one treatment recommendation, in accordance with an embodiment of the present invention, the method having more detail than the method of FIG. 3.

With reference to FIG. 4, a flow diagram is illustrated that shows a method 400 for utilizing time-to-positivity associated with a blood culture to generate at least one treatment recommendation, in accordance with an embodiment of the present invention, the method having more detail than the method of FIG. 3. Initially, as indicated at block 402, a time that the blood sample used to generate a blood culture was taken is received. Subsequently, a time that the blood culture was inoculated, that is, into the culture media, is received. This is indicated at block 404. Next, an indication and time that the blood culture has been received by a positivity-detecting instrument (e.g., positivity-detecting instrument 218 of FIG. 2) is received, as indicated at block 406. Each of the time the blood sample was taken, the time the blood culture was inoculated, and the time the blood culture was received by the positivity-detecting instrument may be received, for instance, by time-receiving module 204 of FIG. 2. Subsequently, as indicated at block 408, an indication that the blood culture is positive for a particular bacterium is received, for instance, by positivity-detecting instrument 218 of FIG. 2, as is the time the blood culture positivity indication was received, e.g., by time-receiving module 204. Subsequently, as indicated at block 410, an indication that the blood culture positivity indication has been verified, for instance, by a laboratory technologist or the like, is received, as is the time the blood culture positivity verification was received.

Next, as indicated at block 412, the time-to-positivity for the presence of the particular bacterium in the blood culture is determined, e.g., utilizing determining module 206 of FIG. 2. By way of example only, and not limitation, the time-to-positivity may be determined by determining a difference between the time at which a blood culture generates a positive result for the presence of the particular bacterium and the time at which the blood sample utilized to generate the blood sample was taken, a difference between the time at which a blood culture generates a positive result for the presence of the particular bacterium and the time at which the blood culture was inoculated, and a difference between the time at which a blood culture generates a positive result for the presence of the particular bacterium and the time at which the blood culture is received by a positivity-detecting instrument (e.g., positivity-detecting instrument 218). Any and all such variations are contemplated to be within the scope of embodiments hereof.

Next, as indicated at block 414, it is determined whether or not the source of the blood sample is known. The source of the blood draw may be, for instance, peripheral or from a central line. It will be appreciated by those of ordinary skill in the art, for instance, that a single positive result for a particular bacterium (e.g., coagulase negative Staphylococcus) in a blood sample taken peripherally may require a different treatment recommendation than the same positive result in a blood sample taken from a central line. If it is determined that the source of the blood sample is not known, at least one treatment recommendation utilizing the determined time-to-positivity is generated, as indicated at block 416. For instance, if a result with the meaning of Gram Positive Cocci is entered in a gram stain report and the determined time-to-positivity is less than nine hours, a treatment recommendation may be generated to change from a broad spectrum therapy to the recommended target antibiotic and a more definitive diagnostic test. Alternatively, if a result with the meaning of Gram Positive Cocci is entered in a gram stain report and the time-to-positivity is equal to or greater than eighteen hours, a treatment recommendation may be generated to discontinue the current antibiotic therapy.

If, however, it is determined that the source of the blood sample is known, an indication of such source is received (e.g., by source-receiving module 208 of FIG. 2) and at least one treatment recommendation utilizing the determined time-to-positivity and the source of the blood sample is generated. This is indicated at block 418. For instance, if a result with the meaning of Gram Positive Cocci is entered in a gram stain report and the source of the specimen is a central line and the time-to-positivity is less than nine hours, a treatment recommendation may be generated to order a quantitative blood culture. It will be understood and appreciated by those of ordinary skill in the art that treatment recommendations may be generated utilizing a variety of methods including, without limitation, best practices. Embodiments of the present invention are not limited to any particular method for generating treatment recommendations based upon the indicated data.

Subsequently, as indicated at block 420, an alert is generated indicating that at least one treatment recommendation has been generated. Such alert may, for instance, be audible and/or visual and may be forwarded to the diagnosing physician at an office computer (e.g., remote computing device 224) so that s/he may determine if a treatment change is desired.

Figure 5:
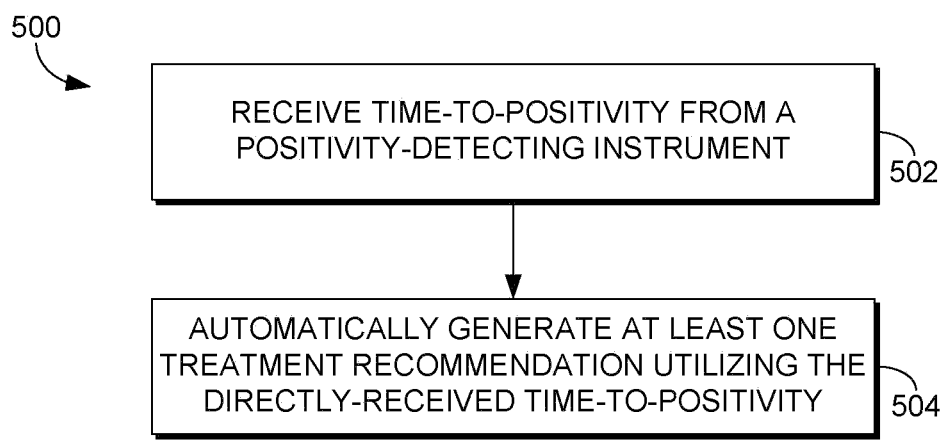
FIG. 5 is a flow diagram illustrating a method for utilizing a time-to-positivity determination taken directly from a positivity-detecting instrument to generate at least one treatment recommendation, in accordance with an embodiment of the present invention.

Turning now to FIG. 5, a flow diagram is illustrated that shows a method 500 for utilizing a time-to-positivity determination taken directly from a positivity-detecting instrument to generate at least one treatment recommendation. By way of example only, such positivity-detecting instrument may be equipped with an associated determining module, obviating the need for (or intended to be used in conjunction with) determining module 206 of FIG. 2. Initially, as indicated at block 502, a time-to-positivity from a positivity-detecting instrument is received. Subsequently, at least one treatment recommendation is automatically generated utilizing the directly-received time-to-positivity. This is indicated at block 504.

Figure 6:
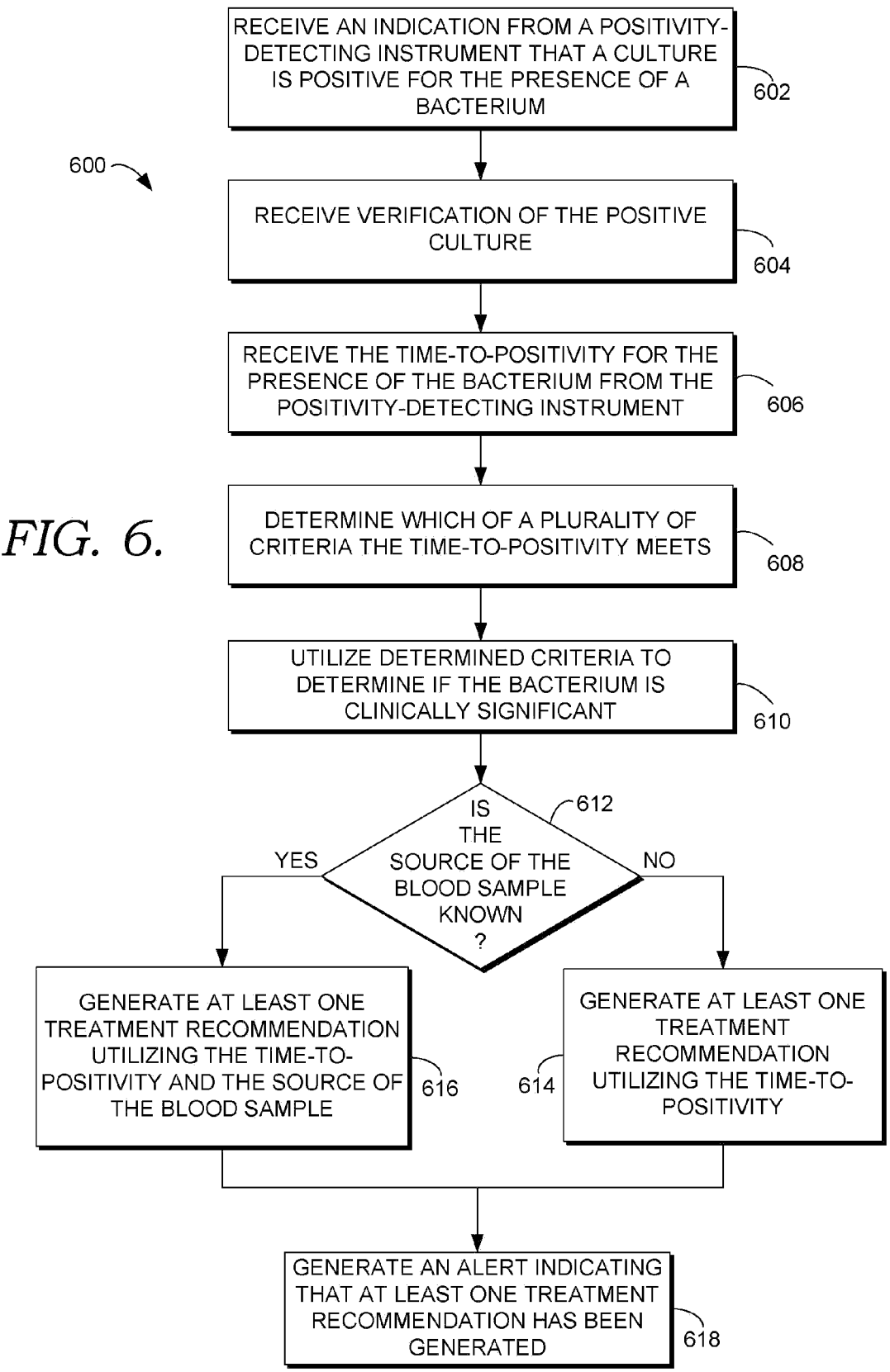
FIG. 6 is a flow diagram illustrating a method for utilizing a time-to-positivity determination taken directly from a positivity-detecting instrument to generate at least one treatment recommendation, in accordance with an embodiment of the present invention, the method having more detail than the method of FIG. 5.

With reference to FIG. 6, a flow diagram is illustrated that shows a method 600 for utilizing a time-to-positivity determination taken directly from a positivity-detecting instrument to generate at least one treatment recommendation, in accordance with an embodiment of the present invention, the method having more detail than the method of FIG. 5. Initially, as indicated at block 602, an indication is received from a positivity-detecting instrument that a blood culture is positive for the presence of a particular bacterium. Subsequently, as indicated at block 604, verification of the positive culture is received, e.g., utilizing verification-receiving module 210 of FIG. 2. Subsequently, a time-to-positivity for the presence of a bacterium is received from the positivity-detecting instrument (e.g., positivity-detecting instrument 218 of FIG. 2). This is indicated at block 606. Next, as indicated at block 608, it is determined which of a plurality of criteria is met by the received time-to-positivity. For instance, each of the plurality of criteria may indicate a particular time frame, e.g., if time-to-positivity is less than four hours it meets criteria one, if time-to-positivity is between four and eight hours it meets criteria two, etc. Once it is determined which of the plurality of criteria is met by the time-to-positivity, the determined criterion is utilized to determine if the bacterium is clinically significant. This is indicated at block 610. By way of example, if the time-to-positivity is less than four hours, that is, it meets criterion one, the bacterium may be determined to be of clinical significance, whereas if the time-to-positivity is between four and eight hours, that is, it meets criterion two, the bacterium may be determined to not be of clinical significance.

Next, as indicated at block 612, it is determined whether or not the source of the blood sample is known. For instance, the blood sample may have been taken peripherally or through a central line. If the source of the blood sample is not known, at least one treatment recommendation is generated utilizing the determined clinical significance (or lack thereof) and the time-to-positivity. This is indicated at block 614. For instance, if a result with the meaning of Gram Positive Cocci is entered in a gram stain report and the determined time-to-positivity is less than nine hours, a treatment recommendation may be generated to change from a broad spectrum therapy to the recommended target antibiotic and a more definitive diagnostic test. Alternatively, if a result with the meaning of Gram Positive Cocci is entered in a gram stain report and the time-to-positivity is equal to or greater than eighteen hours, a treatment recommendation may be generated to discontinue the current antibiotic therapy.

If, however, the source of the blood sample is known, at least one treatment recommendation is generated utilizing the determined clinical significance (or lack therof), the time-to-positivity, and the source of the blood sample. This is indicated at block 616. For instance, if a result with the meaning of Gram Positive Cocci is entered in a gram stain report and the source of the specimen is a central line and the time-to-positivity is less than nine hours, a treatment recommendation may be generated to order a quantitative blood culture.

Once a treatment recommendation has been generated, an alert is generated which indicates such, as indicated at block 618. The alert may be, for instance, an audible alert, a visual alert, or any combination thereof. The alert may additionally be communicated to various health care personnel as desired. The health care personnel recipient(s) may subsequently determine whether or not to follow the recommendation(s).

In operation, by way of example only, suppose a seventy-year-old female is re-admitted to a health care facility with a high fever and shaking chills three days after discharge. A peripheral blood specimen is drawn at 6:00 am in the emergency room and inoculated into two blood culture media. The patient is started on an IV with broad spectrum antibiotic therapy. The blood culture media is delivered to the microbiology laboratory and placed in a positivity-detecting instrument at 6:32 am. At 1:35 pm, the instrument indicates that both culture media are positive. The calculated time-to-positivity is seven hours and three minutes. The microbiologist performs a gram stain and finds that the blood reveals a Gram Positive Cocci in clusters and verifies the result in an electronic health care system. The time-to-positivity, the source of the specimen, and the gram stain result are stored in association with the patient's electronic medical record. Based upon the above data, the act of result verification generates a treatment recommendation for more targeted therapy for a Staphylococcal infection. This recommendation may then be communicated in the form of an alert, as desired.

In another example, suppose a thirty-five-year-old male is admitted to a health care facility with a fever of unknown origin. A peripheral blood specimen is drawn at 5:22 pm in the emergency room and inoculated into two blood culture media. The patient is started on an IV with broad spectrum antibiotic therapy. The blood culture media is delivered to the microbiology laboratory and placed in a positivity-detecting instrument at 6:00 pm. At 2:35 pm the following day, the instrument indicates that one bottle of the media is positive. The calculated time-to-positivity is twenty hours and thirty-five minutes. The microbiologist performs a gram stain and finds that the blood reveals a Gram Positive Cocci in clusters and verifies the result in an electronic health care system. The time-to-positivity, the source of the specimen, and the gram stain result are stored in association with the patient's electronic medical record. Based on the above data, the act of result verification generates a treatment recommendation to discontinue the antibiotic therapy, as the bacterium is considered a contaminant. This recommendation may then be communicated in the form of an alert, as desired.

As can be understood, embodiments of the present invention provide computerized methods and systems, and computer-readable media having computer-executable instructions embodied thereon, for utilizing a time-to-positivity associated with a blood culture to generate at least one treatment recommendation Embodiments of the present invention further provide computerized methods and systems, and computer-readable media having computer-executable instructions embodied thereon, for communicating positivity determinations as appropriate, e.g., utilizing alerts. Utilizing embodiments of the present invention, physicians and other health care personnel are enabled to provide more appropriate therapy, or discontinue inappropriate therapy, which not only reduces the costs of care but also reduces the exposure of organisms to antibiotics, which exposure can cause selective pressure towards antibiotic resistance. In an era of declining health care reimbursements, and in light of increased rates of antibiotic resistance, improving the time to appropriate therapy is desirable.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and within the scope of the claims.

What is claimed is:

1. A method for utilizing a time-to-positivity associated with a blood culture to generate treatment recommendations, the method comprising:

receiving an indication that the blood culture is inoculated and an indication of a first time corresponding to a time at which the blood culture is inoculated;

receiving an indication that the blood culture is received by a positivity-detecting instrument and an indication of a second time corresponding to a time at which the blood culture is received by the positivity-detecting instrument;

at a computing device, receiving, directly from the positivity-detecting instrument, an indication that the blood culture is positive for a presence of a bacterium and an indication of a third time corresponding to a time at which the blood culture generated a positive result for the presence of the bacterium;

determining, at a processor of the computing device, the time-to-positivity for the presence of the bacterium to provide a first determined time-to-positivity, wherein the first determined time-to-positivity is a quantity of time to generate a detectable positive indication of the presence of the bacterium, the quantity of time comprising at least one of a difference between the third time and the first time or a difference between the third time and the second time;

automatically generating at least two treatment recommendations as a first subset of a plurality of treatment recommendations based on the first determined time-to-positivity, wherein the first subset of the plurality of treatment recommendations based on the first determined time-to-positivity is different from a second subset of the plurality of treatment recommendations based on a second time-to-positivity that is different from the first determined time-to-positivity; and in response to automatically generating the at least two treatment recommendations, automatically generating at least one alert indicating that the at least two treatment recommendations have been generated based on the first determined time-to-positivity.

2. The method of claim 1, further comprising receiving verification of the indication that the blood culture is positive for the presence of the bacterium, wherein automatically generating the at least two treatment recommendations comprises automatically generating the at least two treatment recommendations in response to receiving such verification.

3. The method of claim 1, further comprising:
receiving an indication that a blood sample that was utilized to generate the blood culture was taken; and
receiving a fourth time, the fourth time indicating a time at which the blood sample utilized to generate the blood culture was taken,
wherein the quantity of time comprises at least one of a difference between the third time and the first time, a difference between the third time and the second time, or a difference between the third time and the fourth time.

4. The method of claim 1,
wherein if the quantity of time meets at least one first criterion, the method further comprises determining that the bacterium is clinically significant,
wherein if the quantity of time meets at least one second criterion, the method further comprises determining that the bacterium is not clinically significant, and
wherein the first subset of the plurality of treatment recommendations differs depending on whether it is determined that the bacterium is clinically significant or not clinically significant.

5. The method of claim 1, further comprising receiving an indication of a source of a blood sample that is used to provide the blood culture, the source comprising at least one of a peripheral line, a central line, or a venous draw, and wherein automatically generating the at least two treatment recommendations is based on the first determined time-to-positivity and the source of the blood sample.

6. One or more non-transitory computer-storage media having computer-executable instructions embodied thereon that, when executed, cause one or more computing devices to perform a method for utilizing a time-to-positivity associated with a blood culture to generate treatment recommendations, the method comprising:
receiving an indication that the blood culture is inoculated and an indication of a first time, the first time corresponding to a time at which the blood culture is inoculated;
receiving an indication that the blood culture is received by a positivity-detecting instrument and an indication of a second time, the second time corresponding to a time at which the blood culture is received by the positivity-detecting instrument;
receiving, directly from the positivity-detecting instrument, a third time, the third time indicating a time at which an indication that the blood culture is positive for a presence of a bacterium is received by the positivity-detecting instrument;
automatically determining a first time-to-positivity for the presence of the bacterium associated with the blood culture, wherein the first time-to-positivity is at least one of a difference between the third time and the first time or a difference between the third time and the second time; and
automatically generating at least two treatment recommendations as a first subset of a plurality of treatment recommendations based on the first time-to-positivity, wherein the plurality of treatment recommendations is associated with the first time-to-positivity and wherein the first subset of the plurality of treatment recommendations based on the first time-to-positivity is different from a second subset of the plurality of treatment recommendations based on a second time-to-positivity that is different from the first time-to-positivity.

7. The one or more non-transitory computer-storage media of claim 6, wherein the method further comprises:
receiving an indication that a blood sample utilized to generate the blood culture is taken; and
receiving a fourth time, the fourth time indicating a time at which the blood sample utilized to generate the blood culture is taken,
wherein the first time-to-positivity for the presence of the bacterium is determined by calculating at least one of a difference between the third time and the first time, a difference between the third time and the second time, or a difference between the third time and the fourth time.

8. The one or more non-transitory computer-storage media of claim 6,
wherein if the first time-to-positivity meets at least one first criterion, the method further comprises determining that the bacterium is clinically significant,
wherein if the first time-to-positivity meets at least one second criterion, the method further comprises determining that the bacterium is not clinically significant, and
wherein the first subset of the plurality of treatment recommendations differs depending on whether it is determined that the bacterium is clinically significant or not clinically significant.

9. The one or more non-transitory computer-storage media of claim 6, wherein the method further comprises receiving verification of the indication that the blood culture is positive for the presence of the bacterium, wherein automatically generating the at least two treatment recommendations comprises automatically generating the at least two treatment recommendations after such verification is received.

10. The one or more non-transitory computer-storage media of claim 6, wherein the method further comprises automatically generating at least one alert indicating that the at least two treatment recommendations have been generated.

11. The one or more non-transitory computer-storage media of claim 6, wherein the method further comprises receiving an indication of a source of a blood sample utilized to generate the blood culture, the source comprising at least one of a peripheral line, a central line, or a venous draw, wherein automatically generating the at least two treatment recommendations is based the first time-to-positivity and the source of the blood sample.

12. A computing system comprising:
one or more processors; and
computer storage memory having stored thereon computer-executable instructions that, when executed by the one or more processors, implement a method comprising:
receiving, directly from a positivity-detecting instrument, an indication that a blood culture is positive for a presence of a bacterium,
determining a quantity of time associated with generating the indication that the blood culture is positive for the presence of the bacterium, the quantity of time comprising a first time-to-positivity, and
based on the first time-to-positivity, automatically generating at least two treatment recommendations as a first subset of a plurality of treatment recommendations, wherein the first subset of the plurality of treatment recommendations is different from a second subset of the plurality of treatment recommendations, the second subset based on a second time-to-positivity that is different from the first time-to-positivity.

13. The computing system of claim 12, wherein the method further comprises receiving a verification of the presence of the bacterium associated with the blood culture before the at least two treatment recommendations are generated.

14. The computing system of claim 12, wherein the method further comprises automatically generating at least one alert indicating that the at least two treatment recommendations have been generated.

* * * * *